(12) United States Patent
Howard

(10) Patent No.: US 6,602,874 B2
(45) Date of Patent: Aug. 5, 2003

(54) HETEROCYCLIC CARBOXAMIDES

(75) Inventor: Harry R. Howard, Bristol, CT (US)

(73) Assignee: Pfizer Inc., New York, NY (US)

( * ) Notice: Subject to any disclaimer, the term of this patent is extended or adjusted under 35 U.S.C. 154(b) by 63 days.

(21) Appl. No.: 09/862,932

(22) Filed: May 22, 2001

(65) Prior Publication Data

US 2001/0041705 A1 Nov. 15, 2001

Related U.S. Application Data

(62) Division of application No. 09/291,352, filed on Apr. 14, 1999, now Pat. No. 6,277,852.
(60) Provisional application No. 60/081,790, filed on Apr. 15, 1998.

(51) Int. Cl.$^7$ ............... A61K 31/495; A61K 31/50; A61K 31/135
(52) U.S. Cl. ............... 514/252.13; 514/252.14; 514/252.19; 514/252.2; 514/253.09; 514/253.11; 514/254.01; 514/254.02; 514/254.04; 514/254.1; 514/650
(58) Field of Search ............... 514/252.13, 252.14, 514/252.19, 252.2, 253.09, 253.11, 254.01, 254.02, 254.04, 254.1, 650

(56) References Cited

U.S. PATENT DOCUMENTS

| | | | |
|---|---|---|---|
| 4,536,518 A | 8/1985 | Welch et al. | 514/308 |
| 5,130,338 A | 7/1992 | Bacopoulos et al. | 514/646 |

FOREIGN PATENT DOCUMENTS

| | | |
|---|---|---|
| EP | 0343050 | 11/1989 |
| EP | 0434561 | 6/1991 |
| WO | WO9421619 | 9/1994 |
| WO | WO9506044 | 3/1995 |
| WO | WO9531988 | 11/1995 |

OTHER PUBLICATIONS

G. Maura et al., "Serotonin 5–HT1D and 5–HT1A Receptors Respectively Mediate Inhibition of Glutamate Release and Inhibition of Cyclic GMP Production in Rat Cerebellum In Vitro," *J. Neurochemistry*, 66(1), 203–209 (1996).

R. Glennon, "Serotonin Receptors: Clinical Implications," *Neuroscience & Biobehav. Rev.*, 14, 35–47 (1990.).

A. Damasio, "450 Alzheimer's Disease and Related Dementias," in *Cecil Textbook of Medicine*, 18th ed., pp. 2075–2079 (W. B. Saunders, Philadelphia 1992).

A. Goldstein, *Addiction: from Biology to Drug Policy*, pp. 3–5 (W. Freeman & Co. 1994).

*Primary Examiner*—Jerome D. Goldberg
(74) *Attorney, Agent, or Firm*—P. C. Richardson; P. H. Ginsburg; A. D. Joran

(57) ABSTRACT

A compound of the formula

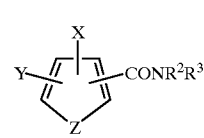

(I)

wherein X, Y, Z, $R^2$ and $R^3$ are as defined above, useful in treating or preventing migraine, depression and other disorders for which a 5-$HT_1$, agonist or antagonist is indicated.

2 Claims, No Drawings

HETEROCYCLIC CARBOXAMIDES

This application is a divisional application of U.S. patent application Ser. No. 09/291,352, now U.S. Pat. No. 6,277,852 filed Apr. 14, 1999, which claims the benefit of U.S. provisional application Ser. No. 60/081,790, filed Apr. 15, 1998.

BACKGROUND OF THE INVENTION

The present invention relates to novel heterocyclic carboxamides to intermediates for their preparation, to pharmaceutical compositions containing them and to their medicinal use. The compounds of the present invention include selective agonists and antagonists of serotonin 1 (5-$HT_1$) receptors, specifically, of one or both of the 5-$HT_{1A}$ and 5-$HT_{1D}$ receptors. They are useful in treating or preventing migraine, depression and other disorders for which a 5-$HT_1$ agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-$HT_1$ agonists and antagonists useful for the treatment of migraine, depression, anxiety, schizophrenia, stress and pain European Patent Publication 343,050, published on Nov. 23, 1989, refers to 7-unsubstituted, halogenated, and methoxy substituted-1-(4-substituted-1-piperazinyl)-naphthalenes as useful 5-$HT_{1A}$ ligand therapeutics.

PCT publication WO 94/21619, published Sep. 29, 1994, refers to naphthalene derivatives as 5-$HT_1$ agonists and antagonists.

PCT publication WO 96/00720, published Jan. 11, 1996, refers to naphthyl ethers as useful 5-$HT_1$ agonists and antagonists.

European Patent Publication 701,819, published Mar. 20, 1996, refers to the use of 5-$HT_1$ agonists and antagonists in combination with a 5-HT re-uptake inhibitor.

Glennon et al., refers to 7-methoxy-1-(1-piperazinyl)-naphthalene as a useful 5-$HT_1$ ligand in their article "5-$HT_{1D}$ Serotonin Receptors", *Drug Dev. Res.*, 22, 25–36 (1991).

Glennon's article "Serotonin Receptors Clinical Implications", *Neuroscience and Behavioral Reviews,* 14, 3547 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Hurtington's disease.

World Patent Application WO 95/31988, published Nov. 30, 1995, refers to the use of a $^5$-$HT_{1D}$ antagonist in combination with a 5-$HT_{1A}$ antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura et al, *J. Neurochem,* 66 (1), 203–209 (1996), have stated that administration of agonists selective for 5-$HT_{1A}$ receptors or for both 5-$HT_{1A}$ and 5-$HT_{1D}$ receptors might represent a great improvement in the treatment of human cerebellar ataxias, a multifaceted syndrome for which no established therapy is available

SUMMARY OF THE INVENTION

The present invention relates to compounds of the formula

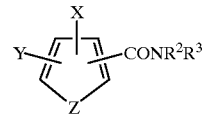

(I)

or the pharmaceutically acceptable salt thereof; wherein

Z is oxygen, S(O)m wherein m is 0, 1 or 2; or NQ wherein Q is hydrogen, ($C_1$–$C_6$)alkyl or phenyl;

X is hydrogen, chloro, fluoro, bromo, iodo, hydroxy, nitro, cyano, ($C_1$–$C_6$)alkyl, trifluoromethyl, ($C_1$–$C_6$)alkoxy, ($C_1$–$C_6$)alkyl S(O), wherein a is 0, 1 or 2; or phenyl wherein the phenyl group is optionally substituted by hydrogen, halo, hydroxy, nitro, cyano, ($C_1$–$C_6$)alkyl, trifluoromethyl, ($C_1$–$C_6$)alkoxy, or ($C_1$–$C_6$)alkyl S(O)b wherein b is 0, 1 or 2;

Y is

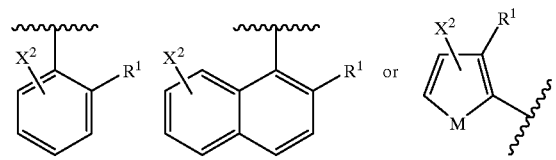

wherein M is oxygen or sulfur;

$X^2$ is hydrogen, fluoro, chloro, trifluoromethyl, ($C_1$–$C_6$) alkyl, ($C_1$–$C_6$)alkoxy or ($C_1$–$C_6$)alkyl S(O), wherein c is 0, 1 or 2;

$R^1$ is a group of the formulas

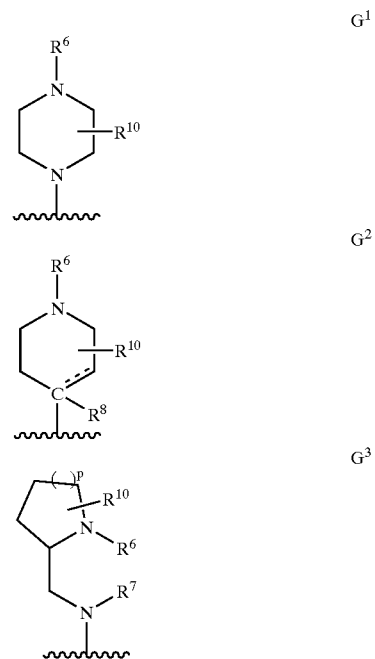

-continued

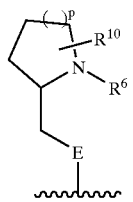
G⁴

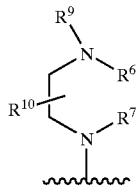
G⁵ or

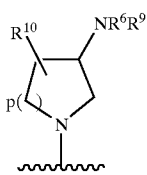
G⁶ wherein the broken line represents an optional double bond;
p is 1, 2 or 3;
E is oxygen or S(O)d wherein d is 0, 1 or 2;
R⁶ is selected from the group consisting of hydrogen, $(C_1-C_6)$alkyl optionally substituted with $(C_1-C_6)$alkoxy or one to three fluorine atoms, or $[(C_1-C_4)$alkyl]aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and $(C_1-C_6)$alkylS$(O)_e$, wherein e is 0, 1 or 2;

R⁷ is selected from the group consisting of hydrogen, $(C_1-C_6)$alkyl, $[(C_1-C_4)$alkyl]aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, —C(=O)—$(C_1-C_6)$alkyl, cyano and $(C_1-C_6)$alkylS$(O)_f$, wherein f is 0, 1 or 2;

or R⁶ and R⁷ taken together form a 2 to 4 carbon chain;
R⁸ is hydrogen or $(C_1-C_3)$alkyl;
R⁹ is hydrogen or $(C_1-C_5)$alkyl;
or R⁶ and R⁹, together with the nitrogen atom to which they are attached, form a 5 to 7 membered heteroalkyl ring that may contain from zero to four heteroatoms selected from nitrogen, sulfur and oxygen;
R¹⁰ is hydrogen or $(C_1-C_6)$alkyl;
R² is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $(C_1-C_6)$alkylS$(O)_g$ wherein g is 0, 1 or 2; and R³ is —$(CH_2)_t$B, wherein t is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, cyano, hydroxy, COOH and $(C_1-C_6)$alkylS$(O)_h$ wherein h is 0, 1 or 2.

The term "alkyl", as used herein, unless otherwise indicated, includes saturated monovalent hydrocarbon radicals having straight, branched or cyclic moieties or combinations thereof.

The term "alkoxy", as used herein, includes 0-alkyl groups wherein "alkyl" is defined above.

Preferred compounds of formula I include those wherein Z is oxygen, S$(O)_m$ wherein m is zero; or NH.

Other preferred compounds of formula I include those wherein Y is a group of the formula

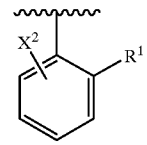

wherein R¹ is 4-methylpiperazin-1-yl and X² is hydrogen, fluoro or chloro.

Other preferred compounds of formula I include those wherein R² is hydrogen, fluoro or chloro.

Other preferred compounds of formula I include those wherein R³ is —$(CH_2)_t$B wherein t is zero or one and B is phenyl or naphthyl wherein the phenyl and naphthyl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, cyano, hydroxy, COOH and $(C_1-C_6)$alkylS$(O)_h$ wherein h is 0, 1 or 2.

More preferred compounds of formula I include those wherein Z is oxygen, S$(O)_m$ wherein m is zero; or NH; Y is a group of the formula

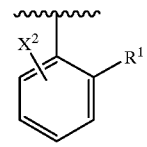

wherein R¹ is 4-methylpiperazin-1-yl and X² is hydrogen, fluoro or chloro; R² is hydrogen, fluoro or chloro; and R³ is —$(CH_2)_t$B wherein t is zero or one and B is phenyl or naphthyl wherein the phenyl and naphthyl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, cyano, hydroxy, COOH and $(C_1-C_6)$alkylS$(O)_h$ wherein h is 0, 1 or 2.

Specific preferred compounds of formula I include the following:

5-[2-(4-methylpiperazin-1-yl)-phenyl]-furan-2-carboxylic acid 4-chlorobenzylamide;

5-[2-(4-methylpiperazin-1-yl)-phenyl]-furan-2-carboxylic acid 4-chlorophenylamide;

5-[2-(4-methylpiperazin-1-yl)-phenyl]-thiophene-2-carboxylic acid 4-chlorophenylamide;

5-[2-(4-methylpiperazin-1-yl)-phenyl]-furan-2-carboxylic acid [2-(4-chlorophenyl)ethyl]-amide;

4-[2-(4-methylpiperazin-1-yl)-phenyl]-furan-2-carboxylic acid 4-chlorobenzylamide;

5-[2-(4-methylpiperazin-1-yl)-phenyl]-thiophene-2-carboxylic acid benzylamide;

5-[2-(4-methylpiperazin-1-yl)-phenyl]-thiophene-2-carboxylic acid 4-fluorobenzylamide;

5-[2-(4-methylpiperazin-1-yl)-phenyl]-thiophene-2-carboxylic acid 4-methoxybenzylamide;

5-[2-(4-methylpiperazin-1-yl)-phenyl]-thiophene-2-carboxylic acid [2-(4-chlorophenyl)ethyl]-amide;

3-methyl-5-[2-(4-methylpiperazin-1-yl)-phenyl]-thiophene-2-carboxylic acid 4-chlorobenzylamide;

5-[5-fluoro-2-(4-methylpiperazin-1-yl)-phenyl]-thiophene-2-carboxylic acid 4-chlorobenzylamide; and 5-[2-(4-methylpiperazin-1-yl)-phenyl]-1H-pyrrole-2-carboxylic acid 4-chlorobenzylamide.

The present invention also relates to a pharmaceutical composition for treating or preventing a disorder or condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g. small cell lung carcinoma), chronic paroxysmal hemicrania and headache (associated with vascular disorders) in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), positraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer, (e.g. small cell lung carcinoma), chronic paroxysmal hemicrania and headache (associated with vascular disorders) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g. small cell lung carcinoma), chronic paroxysmal hemicrania and headache (associated with vascular disorders) in a mammal, preferably a human, comprising a serotonin receptor antagonizing or agonizing effective amount of a compound of the formula I, or a pharmaceutically acceptable salt thereof, and a pharmaceutically acceptable carrier The present invention also relates to a pharmaceutical composition for treating or preventing a disorder or condition that can be treated or prevented by enhancing serotonergic neurotransmission in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a method for treating or preventing a disorder or condition selected from hypertension, depression (e.g., depression in cancer patients, depression in Parkinson's patients, postmyocardial infarction depression, subsyndromal symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette syndrome, trichotillomania, kleptomania, male impotence, cancer (e.g., small cell lung carcinoma), chronic paroxysmal hemicrania and headache (associated with vascular disorders) in a mammal, preferably a human, comprising administering to a mammal requiring such treatment or prevention a serotonin receptor antagonizing or agonizing effective amount of a compound of the formula I or a pharmaceutically acceptable salt thereof.

The present invention also relates to a method for treating or preventing a disorder or condition that can be treated or prevented by enhancing serotonergic neurotransmission in a mammal, preferably a human, comprising administering to a mammal requiring such treatment or prevention a serotonin receptor antagonizing or agonizing effective amount of a compound of the formula I or a pharmaceutically acceptable salt thereof.

The present invention relates to a pharmaceutical composition for treating or preventing a condition or disorder that can be treated or prevented by enhancing serotonergic neurotransmission in a mammal, preferably a human, comprising:

a) a pharmaceutically acceptable carrier;
b) a compound of the formula I or a pharmaceutically acceptable salt thereof; and
c) a 5-HT re-uptake inhibitor, preferably sertraline, or a pharmaceutically acceptable salt thereof;
wherein the amount of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal requiring such treatment or prevention:

a) a compound of the formula I, defined above, or a pharmaceutically acceptable salt thereof; and
b) a 5-HT re-uptake inhibitor, preferably sertraline, or a pharmaceutically acceptable salt thereof;
wherein the amounts of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to said mammal requiring such treatment or prevention:

a) a $5\text{-HT}_{1A}$ antagonist or a pharmaceutically acceptable salt thereof; and
b) a $5\text{-HT}_{1D}$ antagonist of formula I or a pharmaceutically acceptable salt thereof;
wherein the amounts of each active compound (i.e., the $5\text{-HT}_{1A}$ antagonist and the $5\text{-HT}_{1D}$ antagonist) are such that the combination is effective in treating or preventing such disorder or condition.

The present invention also relates to a pharmaceutical composition for treating or preventing a disorder or condition that can be treated or prevented by enhancing serotonergic neurotransmission in a mammal, preferably a human, comprising:

a) a $5\text{-HT}_{1A}$ antagonist or a pharmaceutically acceptable salt thereof; and
b) a $5\text{-HT}_{1D}$ antagonist of formula I or a pharmaceutically acceptable salt thereof;
wherein the amounts of each active compound (i.e., the $5\text{-HT}_{1A}$ antagonist and the $5\text{-HT}_{1D}$ antagonist) are such that the combination is effective in treating or preventing such disorder or condition.

"Enhanced serotonergic neurotransmission," as used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

Sertraline, (1S-cis)4-(3,4-dichlorophenyl)-1,2,3,4-tetrahydro-N-methyl-1-naphthalenamine, as used herein has the chemical formula $C_{17}H_{17}NCl_2$ and the following structural formula

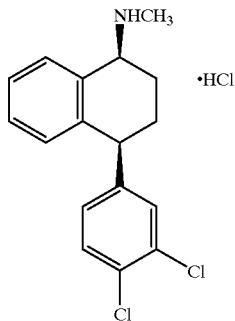

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder and premature ejaculation.

DETAILED DESCRIPTION OF THE INVENTION

The following reaction Schemes illustrate the preparation of the compounds of the present invention. Unless otherwise indicated X, Y, Z, $R^2$ and $R^3$ in the reaction Schemes and the discussion that follow are defined as above

SCHEME 1

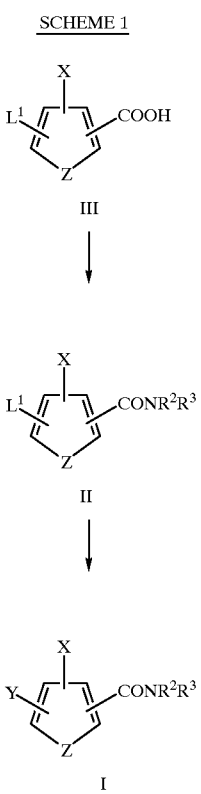

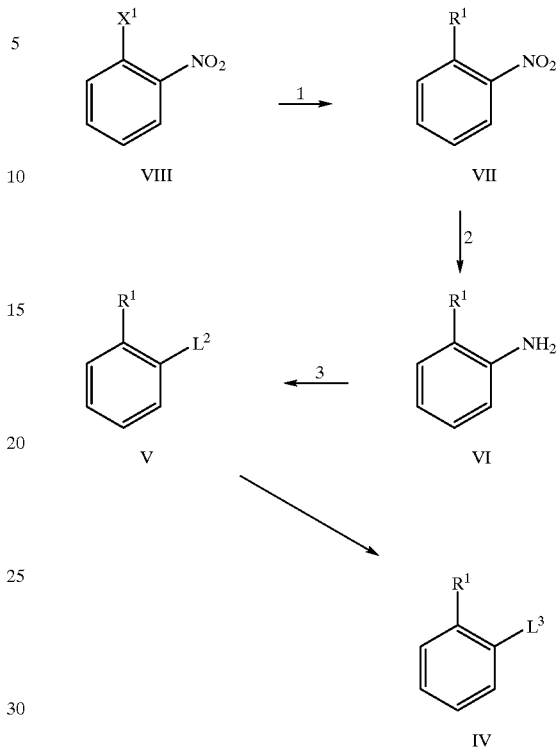

Scheme 1 illustrates a method of synthesizing compounds of formula I wherein $R^1$ is a group of the formula $G^1$ though $G^6$ attached to an aromatic (e.g., phenyl or naphthyl) or heteroaromatic (e.g., thienyl, furanyl) ring. Referring to Scheme 1, step 1, an acid of the formula III is converted to an intermediate which is an amide of formula II using standard techniques known to one skilled in the art, or as described in the chemical literature. For example, Vogel (*Textbook of Practical Organic Chemistry,* 4th edition, Longman Group Ltd., London, 1978) describes the conversion of carboxylic acids to acid chlorides by heating the acid in the presence of phosphorus trichloride, phosphorus pentachloride or thionyl chloride until the conversion is completed; thionyl chloride is the preferred reagent. Similarly, oxalyl chloride in the presence or absence of a suitable reaction inert solvent (e.g., $CHCl_3$ or $CH_2Cl_2$) may be used to prepare the acid chloride which can then be converted to the compounds of formula II by reacting them with an amine of the general formula $HNR^2R^3$ wherein $R^2$ and $R^3$ are as defined. The reaction can be performed in a suitable solvent such as $CHCl_3$ or $CH_2Cl_2$ in the presence or absence of a suitable acid scavenger such as triethylamine (TEA), pyridine, sodium carbonate ($Na_2CO_3$) or potassium carbonate ($K_2CO_3$) and at a temperature of about 0° C. to about the boiling point of the solvent employed.

Alternatively, the acid chloride described above may be reacted with the amino compound of formula $HNR^2R^3$ under Schotten-Baumann conditions in the presence of a suitable base, such as sodium hydroxide, in an aqueous medium and at a convenient temperature of about 0° C. to about 100° C., typically at room temperature, to prepare the amides of formula II.

In another method, the acid of formula III and the amine of formula $HNR^2R^3$ may be converted directly to the compounds of formula II by means of a dehydrating reagent such as dicyclohexylcarbodiimide (DCC), diphenylphosphoryl azide (DPA) or 1-(3-dimethylaminopropyl)-3-ethyl carbodiimide (DEC) in a suitable reaction inert solvent such as tetrahydrofuran (THF) or diethyl ether as described in *Tetrahedron Letters,* 1993, 34, 7685.

In Scheme 1, step 2, the conversion of compounds of formula II to the compounds of formula I may be accomplished by reacting the compounds of formula II, wherein e.g., $L^1$=Br or I, and X is not bromo, iodo or hydroxy, with a compound of the formula IV having a structure as shown in Scheme 2 wherein $L^3$ is a group such as $B(OH)_2$.

Alternatively, compounds of formula II wherein $L^1$=B $(OH)_2$ may be prepared from compounds of formula II, wherein $L^1$ is bromo, X is not bromo, iodo or hydroxy, and neither $R^2$ or $R^3$ is hydrogen, as described above. These latter intermediates of formula II can then be reacted with a compound of the formula V in a similar manner to that described in the preceding paragraph to obtain compounds of formula I.

Scheme 2 illustrates the preparation of compounds of formula IV and V. Compounds of formula V can be prepared from compounds of formula VIII, which are commercially available or readily accessible using standard techniques known to those skilled in the art of synthetic organic chemistry. In Scheme 2, for example, a compound of formula VIII wherein $X^1$ is a leaving group (e.g., F, Cl or Br) can be reacted with an amine, alcohol, or thiol of the formula $R^1H$ to form compounds of the formula VII wherein $R^1$ is $G^1$, $G^3$, $G^4$, $G^5$ or $G^6$. The reaction is generally conducted in the presence or absence of a suitable, reaction inert solvent such as dimethylformamide (DMF) or dimethylfulfoxide (DMSO) at temperatures of about 0° C. to about 160° C., typically the reaction is conducted at room temperature.

The intermediate nitro compound of formula VII can then be converted to an amino compound of formula VI by reduction of the nitro group. This reduction process is well precedented in the literature and can be accomplished using hydrogen gas in the presence of a suitable catalyst such as Raney nickel or palladium on carbon in an inert reaction solvent such as methanol or ethanol at temperatures from about 20° C. to about 60° C. and at pressures of about 1 to about 5 atmospheres of hydrogen. Alternatively, the compounds of formula VII may be converted to compounds of the formula VI using a metal such as tin or zinc in an acidic medium such as hydrochloric acid or acetic acid.

The compound of formula VI may then be converted to the compound of formula V, wherein $L^2$ is a bromine or iodine atom, via a diazonium salt using a process referred to as the Sandmeyer reaction. Conditions for this process are described in Vogel, pages 689–693 and *Chemical Reviews,* 1952, 6, 358 and references contained therein. The diazonium intermediates may also be prepared using compounds of formula VI and alkyl nitrites using a procedure described in *Journal of the Chemical Society,* Section C, 1966, 1249.

Compounds of formula IV can be prepared from the corresponding compounds of formula V, where $L^2$ is for example bromine, using a strong base like n-butyl lithium and a borate ester of formula $B(OR^{11})_3$ wherein $R^{11}$ is lower alkyl as described by D. Reinhoudt et al. *J. Org Chem.,* 1988, 53 (23), 5484. The reaction is carried out in a reaction inert solvent such as 1,2-dimethoxyethane (DME) or tetrahydrofuran (THF) with or without the addition of a small amount of water, using a strong base such as $Na_2CO_3$ in the presence of an amount of a transition metal catalyst such tetrakistriphenylphosphine palladium (0), as described for example in European Patent application 533,268 (published Mar. 24, 1993). Other examples of this coupling reaction may be found in *Tet. Lett.,* 1995, 1679–1682, *Tet. Lett.,* 1985, 5997–6000 and *Heterocycles,* 1992, 34 (7), 1395.

For those compounds of formula I wherein $R^1$=$G^2$ the intermediate of formula V, wherein $R^1$=$G^2$ and $L^2$=Br, can be prepared as described in UK Application 2,083,476 (T Ward, John Wyeth & Bro., published Mar. 24, 1982) and U.S. Pat. No. 2,891,066 (Parke-Davis & Co) and subsequently reacted with the corresponding intermediate of formula II as described above.

Unless indicated otherwise, the pressure of each of the above reactions is not critical Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are useful psychotherapeutics and are potent agonists and/or antagonists of the serotonin 1A (5-$HT_{1A}$) and/or serotonin 1D (5-$HT_{1D}$) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer (e.g. small cell lung carcinoma), chronic paroxysmal hemicrania and headache (associated with vascular disorders).

The affinities of the compounds of this invention for the various serotonin-1 receptors can be determined using standard radioligand binding assays as described in the literature. The 5-$HT_{1A}$ affinity can be measured using the procedure of Hoyer et al. (*Brain Res.*, 376, 85 (1986)). The 5-$HT_{1D}$ affinity can be measured using the procedure of Heuring and Peroutka (*J Neurosci.*, 7, 894 (1987)).

The in vitro activity of the compounds of the present invention at the 5-$HT_{1D}$ binding site may be determined according to the following procedure. Bovine caudate tissue is homogenized and suspended in 20 volumes of a buffer containing 50 mM TRIS•hydrochloride (tris [hydroxymethyl]aminomethane hydrochloride) at a pH of 7.7. The homogenate is then centrifuged at 45,000 G for 10 minutes, The supernatant is then discarded and the resulting pellet resuspended in approximately 20 volumes of 50 mM TRIS•hydrochloride buffer at pH 7.7. This suspension is then pre-incubated for 15 minutes at 37° C., after which the suspension is centrifuged again at 45,000 G for 10 minutes and the supernatant discarded. The resulting pellet (approximately 1 gram) is resuspended in 150 ml of a buffer of 15 mM TRIS•hydrochloride containing 0.01 percent ascorbic acid with a final pH of 7.7 and also containing 10 μM pargyline and 4 mM calcium chloride ($CaCl_2$). The suspension is kept on ice at least 30 minutes prior to use.

The inhibitor, control or vehicle is then incubated according to the following procedure. To 50 μl of a 20 percent dimethylsulfoxide (DMSO)/80 percent distilled water solution is added 200 μl of tritiated 5-hydroxytryptamine (2 nM) in a buffer of 50 mM TRIS•hydrochloride containing 0.01 percent ascorbic acid at pH 7.7 and also containing 10 μM pargyline and 4 μM calcium chloride, plus 100 nM of 8-hydroxy-DPAT (dipropylaminotetraline) and 100 nM of mesulergine. To this mixture is added 750 μl of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters™). The pellet is then washed three times with 4 ml of a buffer of 50 mM TRIS•hydrochloride at pH 7.7. The pellet is then placed in a scintillation vial with 5 ml of scintillation fluid (aquasol 2 ™) and allowed to sit overnight. The percent inhibition can be calculated for each dose of the compound. An $IC_{50}$ value can then be calculated from the percent inhibition values.

The activity of the compounds of the present invention for 5-$HT_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supernate separated and recentrifuged at 70,000 G for 15 minutes. The supernate is discarded and the pellet re-suspended in 10 volumes of 15 mM TRIS•hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS•hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 μm pargyline and kept on ice.

The tissue is then incubated according to the following procedure. Fifty microliters of control, inhibitor, or vehicle (1 percent DMSO final concentration) is prepared at various dosages. To this solution is added 200 μl of tritiated DPAT at a concentration of 1.5 nM in a buffer of 50 mM TRIS•hydrochloride at pH 7.7 containing 4 mM calcium chloride, 0.01 percent ascorbic acid and pargyline. To this solution is then added 750 μl of tissue and the resulting suspension is vortexed to ensure homogeneity. The suspension is then incubated in a shaking water bath for 30 minutes at 37° C. The solution is then filtered, washed twice with 4 ml of 10 mM TRIS•hydrochloride at pH 7.5 containing 154 mM of sodium chloride. The percent inhibition is calculated for each dose of the compound, control or vehicle. $IC_{50}$ values are calculated from the percent inhibition values.

The compounds of formula I of the present invention described in the following Examples were assayed for 5-$HT_{1A}$ and 5-$HT_{1D}$ affinity using the aforementioned procedures. All such compounds of the invention that were tested exhibited $IC_{50}$'s less than 0.60 μM for 5-$HT_{1D}$ affinity and $IC_{50}$'s less than 1.0 μM for 5-$HT_{1A}$ affinity.

The agonist and antagonist activities of the compounds of the invention at 5-$HT_{1A}$ and 5-$HT_{1D}$ receptors can be determined using a single saturating concentration according to the following procedure. Male Hartley guinea pigs are decapitated and 5-$HT_{1A}$ receptors are dissected out of the hippocampus, while 5-$HT_{1D}$ receptors are obtained by slicing at 350 mM on a McIlwain tissue chopper and dissecting out the substantia nigra from the appropriate slices The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 μM GTP and 0.5–1 microcuries of [$^{32}$P]-ATP (30 Ci/mmol. NEG-003—New England Nuclear). Incubation is initiated by the addition of tissue to siliconized microfuge tubes (in triplicate) at 30° C. for 15 minutes. Each tube receives 20 μL tissue, 10 μL drug or buffer (at 10×final concentration), 10 μL 32 nM agonist or buffer (at 10×final concentration), 20 μL forskolin (3 μM final concentration) and 40 μL of the preceding reaction mix. Incubation is terminated by the addition of 100 μL 2% SDS, 1.3 mM cAMP, 45 mM ATP solution containing 40,000 dpm [$^3$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 μM (R)-8-OH-DPAT for 5-HT$_{1A}$ receptors, and 320 nM 5-HT for 5-HT$_{1D}$ receptors. Percent inhibitions by the test compounds are then calculated in relation to the inhibitory effect of (R)-8-OH-DPAT for 5-HT$_{1A}$ receptors or 5-HT for 5-HT$_{1D}$ receptors. The reversal of agonist induced inhibition of forskolin-stimulated adenylate cyclase activity is calculated in relation to the 32 nM agonist effect.

The compounds of the invention can be tested for in vivo activity for antagonism of 5-HT$_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a 5-HT$_{1D}$ agonist, such as [3-(1-methylpyrrolidin-2-ylmethyl)-1H-indol-5-yl]-(3-nitropyridin-3-yl)-amine, (which can be prepared as described in PCT publication WO93/11106, published Jun. 10, 1993) which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The 5-HT$_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin 5-HT$_1$ agonist activity can be determined by the in vitro receptor binding assays, as described for the 5-HT$_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-HT$_{1D}$ receptor using bovine caudate as the receptor source and [$^3$H]serotonin as the radioligand [R. E. Heuring and S. J. Peroutka, *J. Neuroscience*, 7, 894 (1987)]. Of the active compounds tested, all exhibited an IC$_{50}$ in either assay of 1 μM or less.

The compounds of formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5-HT re-uptake inhibitor is referred herein to as "the active combination"), are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive-compulsive disorder, panic disorder, memory disorders (e.g., dementia, amnestic disorders, and age-associated memory impairment), Parkinson's diseases (e.g. dementia in Parkinson's disease, neuroleptic-induced Parkinsonism and tardive dyskinesias), endocrine disorders (e.g. hyperprolactinaemia), vasospasm (particularly in the cerebral vasculature), cerebellar ataxia gastrointestinal tract disorders (involving changes in motility and secretion) chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate): lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 $\mu$g to about 100 mg of the active compound of this invention, preferably from about 1 $\mu$g to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg. to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million (6) and are referenced to the deutenum lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 $\mu$m silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

5-[2-(4-Methylpiperazin-1-yl)-phenyl]-furan-2-carboxylic acid 4-chlorobenzylamide hydrochloride hydrate To a mixture of 5-bromofuran-2-carboxylic acid 4-chlorobenzylamide (0.910 grams. 2.9 mmol) and 2-(4-methylpiperazin-1-yl)-phenylboronic acid (0.5 grams, 2.27 mmol) in 1.2-dimethoxyethane (30 mL) and water (30 mL) was added anhydrous sodium carbonate (0.75 grams, 7.1 mmol) and tetrakis(triphenylphosphine)palladium (0) (0.050 grams, 0.04 mmol, Aldrich Chemical Co.). Under nitrogen, the mixture was heated to 85° C. for 16 hours, at which time a thin layer chromatography (tlc) using methanol: methylene chloride 10:90 showed no starting amide remained. The reaction was cooled to room temperature and concentrated in vacuo to the remove solvents. The residue was absorbed onto silica gel (230–400 mesh) and eluted with methanol: methylene chloride: concentrated $NH_4OH$ (2.5:97.3:0.2). Fractions containing the product (as determined using tlc) were combined and concentrated in vacuc to a clear oil which was dissolved in ether and treated with 4N hydrochloric acid in dioxane to produce the hydrochloride salt, 0.803 grams. Melting point: 110° C. (dec.). Mass spectrum: 410 ($M^{+1}$), 412. $^1$H-NMR ($CDCl_3$, 250 MHz, free base) δ 7.8 (1H, dd), 7.4–7.2 (7H, m), 7.2–7.0 (2H, m), 6.9 (1H, t), 4.7 (2H, d), 3.0 (4H, t), 2.5 (4H, br s), 2.3 (3H, s). Elemental analysis calculated for $C_{23}H_{24}ClN_3O_2.HCl.1.5H_2O$: C, 58.36, H, 5.96, N, 8.88. Found: C, 57.96, H, 5.80,N, 8.86.

The title compounds of Examples 2–13 were prepared by a method analogous to that described in Example 1.

EXAMPLE 2

5-[2-(4-Methylpiperazin-1-yl)-phenyl]-furan-2-arboxylic acid 4-chlorophenylamide hydrochloride hydrate Melting point: 145° C. (dec). Mass spectrum: 396 ($M^{+1}$), 398. $^1$H-NMR ($CDCl_3$, 250 MHz, free base) δ 8.3 (1H, br s), 7.7 (1H, dd), 7.65 (2H, dd), 7.2 (5H, m), 7.1 (2H, m), 3.0 (4H, t), 2.6 (4H, br s), 2.3 (3H, s). Elemental analysis calculated for $C_{22}H_{22}ClN_3O_2.HCl.2.5H_2O$: C, 55.35, H, 5.91, N, 8.80. Found: C, 55.33, H, 5.92. N, 8.59.

EXAMPLE 3

5-[2-(4-Methylpiperazin-1-yl)-phenyl]-thiophene-2-carboxylic acid 4-chlorophenylamide hydrochloride Melting point: 149° C. (dec). Mass spectrum: 412 ($M^{+1}$), 414. $^1$H-NMR ($CDCl_3$, 250 MHz, free base) δ 8.1 (1H, br s), 7.7–7.5 (4H, m). 7.4 (1H, d), 7.3–7.0 (5H, m), 3.0 (4H, t), 2.6 (4H, br s), 2.4 (3H, s).

EXAMPLE 4

5-[2-(4-Methylpiperazin-1-yl)-phenyl]-thiophene-2-carboxylic Acid 4-chlorobenzylamide hydrochloride hydrate Melting point: 256–257° C. Mass spectrum: 426 ($M^{+1}$), 428. $^1$H-NMR ($CDCl_3$, 250 MHz, free base) δ 7.5 (2H, m) 7.4 (1H, d), 7.3 (5H, m), 7.2 (1H, m), 7.1 (1H, m), 6.5 (1H, t), 4.6 (2H, d), 3.0 (4H, t), 2.6 (4H, br s), 2.3 (3H, s). Elemental analysis calculated for $C_{23}H_{24}ClN_3OS.HCl.H_2O$: C, 57.50, H, 5.66, N, 8.75. Found: C, 57.31, H, 5.88, N, 8.64.

EXAMPLE 5

5-[2-(4-Methylpiperazin-1-yl)-phenyl]-furan-2-carboxylic acid 2-(4-chloro-phenethyl)amide Mass spectrum: 424 ($M^{+1}$), 426. $^1$H-NMR ($CDCl_3$, 250 MHz, free base) δ 7.6 (1H, dd), 7.35–7.10 (9H, m), 6.4 (1H, t), 3.65 (2H, q), 2.95 (2H, t), 2.90 (4H, m), 2.6 (4H, br s), 2.4 (3H, s).

EXAMPLE 6

4-[2-(4-Methylpiperazin-1-yl)-phenyl]-furan-2-carboxylic acid 4-chlorobenzylamide Amorphous solid. Mass spectrum: 410 (M$^{+1}$), 412. $^1$H-NMR (CDCl$_3$, 250 MHz, free base) δ 8.05 (1H, s), 7.6 (1H, s), 7.4–7.2 (6H, m), 7.1 (2H, m), 6.7 (1H, m), 4.6 (2H, t), 2.95 (4H, t), 2.5 (4H, br s), 2.3 (3H, s)

EXAMPLE 7

5-[2-(4-Methylpiperazin-1-yl)-phenyl]-thiophene-2-carboxylic acid benzylamide hydrochloride dihydrate Melting point: 145° C. (dec.). Mass spectrum: 392 (M$^{+1}$). $^1$H-NMR (CDCl$_3$, 250 MHz, free base) δ 7.6–7.1 (10H, m), 6.4 (1H, t), 4.6 (2H, d), 3.0 (4H, t), 2.6 (4H, br s), 2.4 (3H, s).

Elemental analysis calculated for C$_{23}$H$_{25}$N$_3$OS.HCl.2H$_2$O: C, 59.53, H, 6.52, N, 9.06. Found: C, 59.39, H. 6.46, N, 8.99.

EXAMPLE 8

5-[2-(4-Methylpiperazin-1-yl)-phenyl]-thiophene-2-carboxylic acid 4-fluorobenzylamide hydrochloride hydrate Melting point: 187–188° C. Mass spectrum: 410 (M$^{+1}$). $^1$H-NMR (CDCl$_3$, 250 MHz, free base) δ 7.5–6.9 (10H, m), 6.4 (1H, t), 4.6 (2H, d), 2.9 (4H, t), 2.5 (4H, br s), 2.4 (3H, s). Elemental analysis calculated for C$_{23}$H$_{24}$FN$_3$OS.HCl.1.25 H$_2$O: C, 58.96, H, 5.92, N, 8.97. Found: C, 58.86, H. 5.81, N, 9.03.

EXAMPLE 9

5-[2-(4-Methylpiperazin-1-yl)-phenyl]-thiophene-2-carboxylic acid 4-methoxy-benzylamide hydrochloride Melting point: 140° C. (dec). Mass spectrum 422 (M$^{+1}$). $^1$H-NMR (CDCl$_3$, 250 MHz, free base) δ 7.5–7.1 (7H, m), 6.9 (2H, br s), 6.4 (1H, t), 4.6 (2H, d), 3.9 (3H, s), 3.0 (4H, t), 2.6 (4H, br s), 2.4 (3H, s). Elemental analysis calculated for C$_{24}$H$_{27}$N$_3$O$_2$S.HCl: C, 60.55, H, 6.35, N, 8.83. Found: C, 60.30, H, 6.42, N, 8.76.

EXAMPLE 10

5-[2-(4-Methylpiperazin-1-yl)-phenyl]-thiophene-2-carboxylic acid 2-(4-chlorophenethyl)amide Amorphous solid. Mass spectrum: 440 (M$^+$), 442. $^1$H-NMR (CDCl$_3$, 250 MHz, free base) δ 7.5 (1H, d) 7.4 (2H, m), 7.2 (3H, m), 7.1 (4H, m), 6.1 (1H, t), 3.7 (2H, t), 3.0 (6H, m), 2.6 (4H, br s), 2.3 (3H, s).

EXAMPLE 11

3-Methyl-5-[2-(4-methylpiperazin-1-yl)-phenyl]-thiophene-2-carboxylic acid 4-chlorobenzylamide Amorphous solid. Mass spectrum. 440 (M$^+$), 442.

EXAMPLE 12

5-[5-Fluoro-2-(4-methylpiperazin-1-yl)-phenyl]-thiophene-2-carboxylic acid 4-chlorobenzylamide monohydrate Melting point: 175–176.5° C. Mass spectrum: 444 (M$^{+1}$). $^1$H-NMR (CDCl$_3$, 250 MHz, free base) δ 7.5 (2H, m), 7.4 (1H, d), 7.3 (5H, m), 7.2 (1H, m), 7.1 (1H, m), 6.5 (1H, t), 4.6 (2H, d), 3.0 (4H, t), 2.6 (4H, br s), 2.3 (3H, s). Elemental analysis calculated for C$_{23}$H$_{23}$ClFN$_3$OS•H$_2$O: C, 59.80, H, 5.45, N, 9.10. Found: C, 59.73, H, 5.38, N, 9.04.

EXAMPLE 13

5-[2-(4-Methylpiperazin-1-yl)-phenyl]-1H-pyrrole-2-carboxylic acid 4-chlorobenzylamide hydrochloride Melting point 80° C. (dec.). Mass spectrum: 409 (M$^{+1}$), 411. $^1$H-NMR (CDCl$_3$, 250 MHz, free base) δ 12.7 (1H, br s), 11.8 (1H, br s), 7.6 (1H,tm), 7.3–7.0 (6H, m), 6.7 (2H, m), 6.5 (1H, m), 4.6 (2H, d), 3.7–3.2 (6H, m+t), 3.1 (2H, d), 2.9 (3H, s).

Preparation 1

2-(4-Methylpiperazin-1-yl)-phenylboronic Acid

In a round bottom flask fitted with a condenser and addition funnel, N-methylpiperazine (10.0 grams, 0.1 mol) was stirred while 2-fluoronitrobenzene (14.1 grams, 0.1 mol) was added dropwise under nitrogen. Caution—a vigorous exotherm occurred when approximately 20% of the 2-fluoronitrobenzene had been added. Following completion of the addition (~30 min.) the reaction was stirred another 60 min. at room temperature, diluted with methylene chloride (100 mL) and washed with saturated aqueous Na$_2$CO$_3$ and saturated aqueous sodium chloride. After drying with MgSO$_4$, the solvent was removed in vacuo to give 2-(4-methylpiperazin-1-yl)-1-nitrobenzene as an orange oil, 20.4 grams. Mass spectrum: 221 (M$^+$), 174 (M-HNO$_2$) $^1$H-NMR (CDCl$_3$, 300 MHz) δ 7.8–7.0 (4H, m), 3.05 (4H, m), 2.55 (4H, t), 2.3 (3H, s).

The preceding oil (45 g) in 400 mL of methanol was treated with 5 g of 10% palladium on carbon and hydrogenated on a Parr shaker apparatus at 50 psi for 2 hr. The catalyst was then removed by filtration though a pad of diatomaceous earth (d.e.) and concentrated to 40 grams of a viscous oil which solidified on standing. Trituration with hexanes gave 2-(4-methylpiperazin-1-yl)-aniline as a pale purple powder, 32.8 grams. Melting point: 94–97° C. Mass spectrum: 191 (M$^+$). $^1$H-NMR (CDCl$_3$, 300 MHz) δ 7.0 (1H, dd), 6.9 (1H, dt), 6.7 (2H, m), 3.95 (2H, br s). 2.95 (4H, t), 2.55 (4H, t), 2.3 (3H, s).

A solution of 2-(4-methylpiperazin-1-yl)-aniline (23.77 grams, 0.124 mol) in 80 mL of 48% hydrobromic acid was cooled to 20° C. and treated with a solution of sodium nitrite (8.6 grams, 0.124 mol) in 35 mL of water while maintaining a temperature of 20–25° C. To this was added a solution of copper (II) bromide (3.5 grams, 0.024 mol) in 12 mL of 48% HBr. The mixture was heated to 85° C. for approximately 30 minutes, poured over crushed ice in a large beaker and neutralized with dilute aqueous sodium hydroxide. The crude product was extracted into diethyl ether and concentrated in vacuo to a black oil which was chromatographed on silica gel using triethylamine.methanol.methylene chloride (0.5:10:90) as the eluent. The product, 1-bromo-2-(4-methylpiperazin-1-yl)benzene, was obtained as a brown oil 20 grams Mass spectrum: 254 (M$^+$), 256 $^1$H-NMR (CDCl$_3$, 300 MHz) δ 7.55 (1H, d), 7.30 (1H, t), 7.05 (1H, d), 6.9 (1H, t), 3.05 (4H, br s), 2.55 (4H, t), 2.35 (3H, s).

A solution of the preceding intermediate (5.1 grams, 0.02 mol) in 50 mL of anhydrous THF under nitrogen was cooled to −78° C., using a dry ice/acetone bath, and treated with 2.5M n-butyl lithium in hexanes (9.0 mL, 0.0225 mol). The resulting slurry was stirred an additional 15 min at −78° C. and treated with trimethyl borate (2.6 mL, 0.0225 mol, Aldrich Chemical Co., Milwaukee, Wis.) in one portion. The reaction flask was removed from the cooling bath and the dark solution was allowed to stir at 25° C. overnight. The mixture was then poured into 200 mL of saturated aqueous NaHCO$_3$ and 100 mL of ethyl acetate, the aqueous layer was extracted with additional volumes of ethyl acetate and the combined organics were washed with saturated aqueous sodium chloride and dried with $MgSO_4$. The ethyl acetate was removed in vacuo to give 2-(4-methylpiperazin-1-yl)-phenylboronic acid as an orange semisolid which was triturated with hexanes and dried to a tan powder, 2.05 grams. Mass spectrum 221 ($M^{+1}$). $^1$H-NMR (CDCl$_3$, 300 MHz) δ 8.9 (2H, br s), 7.95 (1H, d), 7.45 (1H, t), 7.35 (1H, d), 7.25 (1H, t), 3.0 (4H, m), 2.6 (4H, m), 2.35 (3H, s).

Preparation 2

5-bromofuran-2-carboxylic Acid 4-chlorobenzylamide

A solution of 5-bromofuran-2-carboxylic acid (10.2 grams, 53.4 mmol) in 100 mL of methylene chloride was treated with oxalyl chloride (5.0 mL, 57.3 mmol) dropwise over a 10 min period The solution was then treated with 0.2 mL of DMF (Caution—foaming occurs) and stirring continued another 1 hr at room temperature. The solvent was removed in vacuo and the resulting solid acid chloride was dried under vacuum.

The preceding was rediluted in 80 mL of methylene chloride. One half of this solution was treated with triethylamine (3.6 mL, 25.8 mmol), followed by a solution of 4-chlorobenzylamine (3.5 mL, 28.8 mmol) in 10 mL of methylene chloride added dropwise to control the exotherm After stirring overnight at room temperature, 1N hydrochloric acid was added to a pH of approximately 7 and the reaction mixture was filtered through d e. The organic layer was then washed with 1N hydrochloric acid, saturated aqueous $NaHCO_3$, and saturated sodium chloride. After drying over $MgSO_4$ and treating with activated charcoal, the organics were filtered through d.e. and concentrated in vacuo to a brown solid which was recrystallized from ethyl acetate:hexanes as a tan solid, 4.91 grams. Mass spectrum 316 ($M^{+1}$), 318 $^1$H-NMR (CDCl$_3$, 250 MHz) δ 7.3 (4H, m), 7.0 (1H, d), 6.7 (1H, br s), 6.4 (1H, d), 4.5 (2H, d).

The title compounds of Preparations 3–12 were prepared by a method analogous to that described in Preparations 1–2

Preparation 3

5-Bromofuran-2-carboxylic Acid 4-chlorophenylamide

Light tan solid Mass spectrum. 302 ($M^{+1}$), 304. $^1$H-NMR (CDCl$_3$, 250 MHz) δ 8.0 (1H, br s), 7.6 (2H, d), 7.2 (2H, d), 7.1 (1H, d), 6.5 (1H, d).

Preparation 4

5-Bromothiophene-2-carboxylic Acid 4-chlorophenylamide

White solid. Melting point: 192–193° C. Mass spectrum 318 ($M^{+1}$), 320. $^1$H-NMR (CDCl$_3$, 250 MHZ) δ 8.0 (1H, brs), 7.6 (2H, d), 7.2 (2H, d), 7.1 (1H, d), 6.5 (1H, d).

Preparation 5

5-Bromothiophene-2-carboxylic Acid 4-chlorobenzylamide

White solid Melting Point: 142–143° C. Mass spectrum. 332 ($M^{+1}$), 334 $^1$H-NMR (CDCl$_3$, 250 MHz) δ 9.2 (1H, t), 7.6 (1H, d), 7.2 (5H, m), 4.5 (2H, d).

Preparation 6

5-Bromofuran-2-carboxylic Acid 2-(4-chlorophenethyl)amide

Tan solid Mass spectrum 328 ($M^{+1}$), 330, 332.

Preparation 7

4-Bromofuran-2-carboxylic Acid 4-chlorobenzylamide

White amorphous solid. Mas spectrum: 314 ($M^{+1}$), 316, 318.

Preparation 8

5-Bromothiophene-2-carboxylic Acid Benzylamide

White solid. Mass spectrum: 296 ($M^{+1}$), 298 $^1$H-NMR (CDCl$_3$, 250 MHz) δ 7.4 (5H, m), 7.2 (1H, d), 7.0 (1H, d), 6.4 (1H, brs), 4.5 (2H, d).

Preparation 9

5-Bromothiophene-2-carboxylic Acid 4-fluorobenzylamide

White solid. Mass spectrum: 314 ($M^{+1}$), 316. $^1$H-NMR (CDCl$_3$, 250 MHz) δ 7.4–7.2 (3H, m), 7.1 (3H, m), 6.2 (1H, brs), 4.5 (2H, d).

Preparation 10

5-Bromothiophene-2-carboxylic Acid 4-methoxybenzylamide

White solid. $^1$H-NMR (CDCl$_3$, 250 MHz) δ 7.4–7.2 (3H, m), 7.0 (1H, d), 6.9 (1H, q), 6.1 (1 H, br s), 4.5 (2H, d), 3.7 (3H, s).

Preparation 11

5-Bromothiophene-2-carboxylic Acid 2-(4-chlorophenethyl)amide

Yellow solid $^1$H-NMR (CDCl$_3$, 300 MHz) δ 8.65 (1H, t), 7.55 (1H, d), 7.3 (4H. q), 3.40 (2H, m), 3.30 (1H, m), 2.75 (2H, t).

Preparation 12

5-Bromo-3-methylthiophene-2-carboxylic Acid 4-chlorobenzylamide

Yellow solid. Mass spectrum 343 ($M^+$), 345, 347. $^1$H-NMR (CDCl$_3$, 250 MHz) δ 7.4–7.2 (4H, m), 6.9 (1 H, s), 6.0 (1 H, br s), 4.5 (2H, d), 2.45 (3H, s).

What is claimed is:

1. A method for treating or preventing depression in a mammal, comprising administering to mammal in need thereof:

a) a compound of the formula

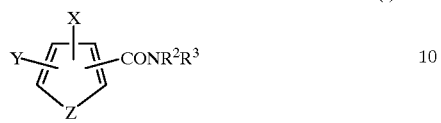

(I)

or the pharmaceutically acceptable salt thereof; wherein

Z is oxygen, $S(O)_m$ wherein m is 0, 1 or 2; or NQ wherein Q is hydrogen, $(C_1-C_6)$alkyl or phenyl;

X is hydrogen, chloro, fluoro, bromo, iodo, hydroxy, nitro, cyano, $(C_1-C_6)$alkyl, trifluoromethyl, $(C_1-C_6)$ alkoxy, $(C_1-C_6)$alkyl $S(O)_a$ wherein a is 0, 1 or 2; or phenyl wherein the phenyl group is optionally substituted by hydrogen, halo, hydroxy, nitro, cyano, $(C_1-C_6)$alkyl, trifluoromethyl, $(C_1-C_6)$alkoxy, or $(C_1-C_6)$alkyl $S(O)_b$ wherein b is 0, 1 or 2;

Y is

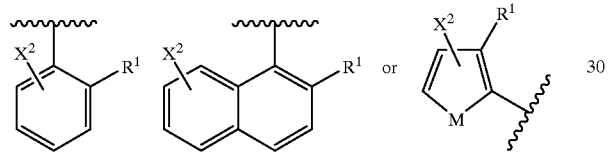

wherein M is oxygen or sulfur;

X is hydrogen, fluoro, chloro, trifluoromethyl, $(C_1-C_6)$ alkyl, $(C_1-C_6)$alkoxy or $(C_1-C_6)$alkyl $S(O)_c$ wherein c is 0, 1 or 2;

$R^1$ is $G^1$

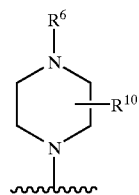

$R^6$ is selected from the group consisting of hydrogen, $(C_1-C_6)$alkyl optionally substituted with $(C_1-C_6)$ alkoxy or one to three fluorine atoms, or $[(C_1-C_4)$ alkyl] aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chioro, fluoro, bromo, iodo, $(C_1-C_6)$alkyl, $(C_1-C_6)$alkoxy, trifluoromethyl, cyano and $(C_1-C_6)$alkylS$(O)_e$, wherein e is 0, 1 or 2;

$R^{10}$ is hydrogen or $(C_1-C_6)$alkyl;

$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $(C_1-C_6)$alkylS$(O)_g$ wherein g is 0, 1 or 2; and $R^3$ is —$(CH_2)_t$B, wherein t is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, COGH and $(C_1-C_6)$alkylS$(O)_h$ wherein h is 0, 1 or 2; and b) sertraline or a pharmaceutically acceptable salt thereof wherein the amounts of a) and b) are such that the combination is effective in treating or preventing depression."

2. A pharmaceutical composition for treating or preventing depression in a mammal comprising amounts of a) a compound of formula 1 according to claim 1 and b) sertraline or pharmaceutically acceptable salt thereof; wherein the amounts of a) and b) are such that the combination is effective in treating or preventing depression.

* * * * *